United States Patent [19]

ElSohly et al.

[11] Patent Number: 5,618,538

[45] Date of Patent: Apr. 8, 1997

[54] METHODS AND COMPOSITIONS FOR ISOLATING TAXANES

[75] Inventors: Hala N. ElSohly; Edward M. Croom, Jr.; Mahmoud A. ElSohly, all of Oxford; James D. McChesney, Etta, all of Miss.

[73] Assignee: The University of Mississippi, University, Miss.

[21] Appl. No.: 470,746

[22] Filed: Jun. 6, 1995

Related U.S. Application Data

[62] Division of Ser. No. 95,817, Jul. 21, 1993, Pat. No. 5,480,639, which is a continuation of Ser. No. 690,805, Apr. 19, 1991, abandoned.

[51] Int. Cl.$^6$ .................................................. A61K 35/78
[52] U.S. Cl. ...................... 424/195.1; 514/449; 514/510
[58] Field of Search ..................... 424/195.1; 514/449, 514/510

[56] References Cited

U.S. PATENT DOCUMENTS

| | | | |
|---|---|---|---|
| 4,206,221 | 6/1980 | Miller et al. | 514/471 |
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 5,019,504 | 5/1991 | Christen et al. | 435/123 |

FOREIGN PATENT DOCUMENTS

| | | |
|---|---|---|
| 0253738 | 1/1988 | France . |
| 0253739 | 1/1988 | France . |

OTHER PUBLICATIONS

Vidensek, N., et al., Taxol Content in Bark, Wood, Root, Leaf, Twig, and Seedling From Several Taxus Species, Journal of Natural Products (1990) 53(6): 1609–1610.

National Products Branch, National Cancer Institute, description of taxol dated Jul. 15, 1983.

Bailey, et al., A Concise Dictionary of Plants Cultivated in the United States and Canada. Hortus Third (1976), pp. ix–xiii AND 1098–1099.

Harvey, S.D., et al., Separation of Taxol From Related Taxanes in Taxus Brevifolia Extracts by Isocratic Elution Reversed-Phase Microcolumn High-Performance Liquid Chromatography. Journal of Chromatography (1991) 587: 300–305.

McLaughlin, J.L., et al., 19–Hydroxybaccatin III, 10–Deacetylcephalomannine, and 10–Deacetyltaxol: New Anti–Tumor Taxanes From Taxus Wallichiana. Journal of Natural Products (1981) 44:312–319.

Miller, R.W., A Brief Survey of Taxus Alkaloids and Other Taxane Derivatives. J. Natural Prod. (1980) 43(4): 425–437.

Miller, R.W., et al., Antileukemic Alkaloids From Taxus Wallichiana Zucc. J. Organic Chemistry (1981) 46: 1469–1474.

Rowinsky, E.K., et al., Taxol: A Novel Investigational Antimicrotubule Agent. Journal of the National Cancer Institute (1990) 82(15); 1247–1259.

Senilh, V., et al., Mise En Evidence De Nouveaux Analogues Du Taxol Extraits De Taxus Baccata. Journal of Natural Products (1984) 47: 131–137.

Vanhaelen–Fastre, R., et al., High–Speed Countercurrent Chromatography Separation of Taxol and Related Diterpenoids From Taxus Baccata. Journal of Liquid Chromatography (1992) 15(4): 697–706.

Wani, et al., Plant Antitumor Agents, VI. The Isolation and Structure of Taxol, a Novel Antileukemic and Antitumor Agent from Taxus brevifolia, J. American Chemical Society (1971) 93(9): 2325–2327.

Withrup, K.M., et al., High Performance Liquid Chromatographic Separation of Taxol and Related Compounds From Taxus brevifolia. Joural of Liquid Chromatography (1989) 12(11): 2117–2132.

Witherup, K.M., et al., Taxus Spp. Needles Contain Amounts of Taxol Comparable to the Bark of Taxus Brevifolia: Analysis and Isolation. Journal of Natural Products (1990) 53(5): 1249–1255.

Zongping Zhang, et al., New Taxanes from Taxus Chinensis. Planta Medica (1990) 56: 293–294.

*Primary Examiner*—John W. Rollins
*Attorney, Agent, or Firm*—John P. White

[57] ABSTRACT

Methods of obtaining renewable sources of taxanes including taxol are provided. Compositions comprising taxanes which are useful as source materials for the further purification of taxanes are also disclosed. Specifically, a method of drying plant matter to preserve their taxane content and facilitate their extraction is disclosed. In addition, methods of extracting and purifying taxol and other taxanes from ornamental cultivars using a series of organic and aqueous solvents and normal phase chromatography columns are also disclosed.

5 Claims, No Drawings

METHODS AND COMPOSITIONS FOR ISOLATING TAXANES

This application is a divisional of U.S. Ser. No. 08/095,817, filed Jul. 21, 1993 now U.S. Pat. No. 5,480,639 which is a continuation of U.S. Ser. No. 07/690,805, filed Apr. 19, 1991 now abandoned.

TECHNICAL FIELD OF THE INVENTION

This invention relates to methods and compositions for obtaining crude taxane mixtures from renewable sources of plant matter and a method of purifying such taxane mixtures and compositions to obtain specific taxanes. More particularly, this invention relates to a method of treating plant matter in a manner which preserves taxane content. This invention also relates to a method of extracting taxanes from plant matter with solvents to produce a crude mixture of taxanes wherein the crude taxane mixture is present in an aqueous solvent. Additionally, this invention relates to a method of purifying specific taxanes from a crude taxane mixture using normal phase chromatography.

BACKGROUND OF THE INVENTION

Taxanes are alkaloids possessing a taxane nucleus. The taxane nucleus comprises the three ring structure shown below which is also identified as 4,8,12,15,15-pentamethyl-tricyclo [9.3.1.0$^{3,8}$] pentadecane.

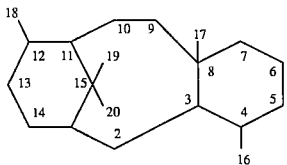

At least 56 different taxanes have been identified in the literature. For example, in 1980, R. W. Miller authored an article which surveyed known taxus alkaloids and other taxane derivatives and reported for these compounds formulas, HNMR, MS, and x-ray data. The article by R. W. Miller, appearing at *J. Nat. Prod.* 43(4): 425–437 (1980) is incorporated herein by reference. The following publications which are also incorporated herein by reference identify and describe taxanes. M. G. Begley, E. A. Freeknall, and G. Pattenden, *Acta Crystallogr,* 40; 1745 (1984); D. P. Della Casa de Marcano and T. G. Halsall, Chem. Comm. 1382 (1970); D. G. I. Kingston, D. A. Hawkins, and L. Ovington, *J. Nat. Prod.* 45; 466 (1982); F. Gueritte-Voeglein, D. Gu énard, and P. Potter. *J. Nat. Prod.* 50:(1):9–11 (1987); B. Lythgoe in "The Alkaloids" Ed. by R. H. F. Manske, Vol. 10, Academic Press, New York 1968, pp. 597–626; D. P. Della Casa de Marcano and T. G. Halsall, *Chem. Commun.* 1381 (1970); V. Senilh, S. Blechert, M. Colin, D. Guenard, F. Picot, P. Potier, and P. Varenne, *J. Nat. Prod.* 47(1) pp. 131–137 (1984); J. L. McLaughlin, R. W. Miller, R. G. Powell and C. R. Smith, Jr., *J. Nat. Prod.* 44:312–19 (1981); D. P. Della Casa de Marcano and T. G. Halsall, Chem. Comm. 365 (1975); C. H. Oliver Huang, David G. I. Kingston, Neal F. Magri, G. Samaranayake and F. E. Boetner, *J. Nat. Prod.* 49(4): 665–669 (1986).

The taxane series of molecules possess potent antitumor activity. Generally, the taxanes which have been studied for their antitumor activity have found use in the treatment of ovarian cancer and leukemia (W. P. MacGuire et al., *Annals of Internal Medicine,* vol. 111, pg. 273 (1989)). Taxanes are believed to exert their antitumor activity by inducing tubulin polymerization and forming extremely stable and nonfunctional microtubules which has an antiproliferative effect on taxane sensitive cells. (Eric K. Rowinsky et al., *Journal of the National Cancer Institute,* Vol. 82, No. 15, pp. 1247–1259 (1990)). Among the taxane molecules which have been studied most with respect to their antitumor activity are taxol, cephalomannine, desacetylcephalomannine, baccatin III, 10-desacetyl baccatin III and 10-desacetyltaxol. The structures of these taxanes are shown below:

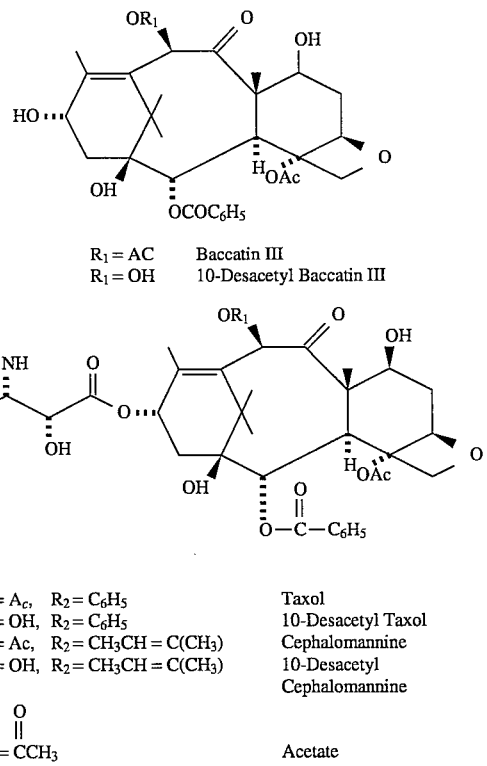

The taxane compound known as taxol, was first reported to be isolated from the stem bark of the western yew *Taxus brevifolia,* a slow growing conifer. Its structure was elucidated by M. C. Wani et al., *Journal of the American Chemical Society,* Vol. 93, pp. 2325–2327, (1971).

Taxanes are commonly isolated from the bark of *T. brevifolia* collected in the wild. Because the concentration of specific taxanes in *T. brevifolia* is extremely low (for example, taxol is present in a concentration of between about 0.004% to about 0.02% based upon the dry weight of bark), large quantities of trees must be harvested and processed to produce even modest amounts of taxanes needed for research purposes. Furthermore, wild trees grow under very different conditions resulting in highly variable levels of taxanes produced in the bark. In addition, wild populations of trees are an unreliable source for taxanes because they are plagued with many uncertainties and risks such as forest fires, annual climatic variations, natural variations in taxol content in the different chemotypes of wild populations. Increased criticism from environmentalists concerning harvesting of wild plants also threatens the availability of *T. brevifolia* as an adequate source of taxanes. *T. brevifolia,* therefore, represents a nonrenewable and inconsistent source of taxanes.

Even more critical is the fact that extensive harvesting of wild trees risks the destruction of the germplasm essential for the future cultivation of *T. brevifolia*. Such harvesting could result in the loss of wild genes coding for proteins providing for such characteristics as disease and pest resistance, cold hardiness, high growth rates and tolerance to full sunlight and the extremes of drought and flooding and high taxol/taxane content. The preservation of these wild genes will be critical to long-term development of cost-effective taxol and other taxane production whether produced from cultivated plants, tissue culture or genetically modified microorganisms. Because of the critical role wild germplasm will serve in future production strategies, the preservation of wild populations should be considered an essential component of the development strategy for taxol and other taxane production.

Since the harvesting of wild populations of *T. brevifolia* yields such a limited supply of taxol, clinical experiments of taxol have been restricted to only a few specific chemotherapeutic applications. Lack of a stable and reliable source of taxol at a predictable cost will also significantly impede clinical utilization of the agent. Development of a sustainable, economic and reliable source for taxanes is imperative.

The potential of taxol as a cancer chemotherapeutic agent and the structural complexity of the taxol molecule has prompted a large effort directed toward its de novo synthesis. However, the molecular complexity of taxol suggests that a total synthesis of taxol from readily available raw material is not likely to be economically feasible.

A synthesis of the taxane ring skeleton is reported by R. A. Holton et al., at *Journal of the American Chemical Society*, 106 5731 (1984), and ibid, Vol. 110, pp. 6558–6560 (1988). However, these syntheses are deficient in that the final product lacks sufficient pharmacological activity to serve as an effective antitumor agent.

Semi-synthesis of taxol using 10-desacetyl baccatin III, a more abundant precursor isolated from the leaves of *T. baccata* (1 g/Kg fresh leaves), has been reported by French workers. Additionally, V. Senilh et al., *C. R. Seances Acad. Sci.* Ser. 2, Vol. 299, pp. 1039–1043 (1984); F. Gueritte-Voegelin, *Tetrahedron*, Vol. 42, pp. 4451–4460 (1986); Colin et al. European patent application 0 253 278 and Colin et al. European patent application 0 253 739 refer to the semisynthesis of taxol from 10-desacetyl baccatin III. These methods use taxane derivatives as the starting materials, and, therefore, suffer from the disadvantage that the approach requires isolation and purification of taxanes from a plant source followed by conversion of the purified taxane to taxol; this multistage preparation of taxol is more expensive than isolation of taxol directly from the plant material.

There have been efforts to develop new techniques for isolating taxanes such as taxol from plant matter. However, none of the methods reported to date provide for the adequate extraction of taxanes from a renewable source. For example, M. C. Wani et al., *Journal of the American Chemical* Society, Vol. 93, pp. 2325–2327 (1971), refers to the purification of taxanes from stem bark of *Taxus brevifolia* using normal phase column chromatography protocols. Normal phase column chromatography entails the use of a polar column packing to effect molecular separation.

National Cancer Institute Natural Products Branch paper NSC #125973 dated Jul. 15, 1983 also refers to the purification of taxol from bark, wood without bark, branches, twigs, needles, seeds/fruits and roots also from *Taxus brevifolia*.

A disadvantage of the method for isolating taxol described in the NSC #125973 paper and other publications is the reliance on the use of methylene chloride in the extraction process. Methylene chloride and other chlorinated hydrocarbons, such as chloroform, are recognized to be toxic and potentially carcinogenic. It is, therefore, desirable to avoid utilizing these solvents in the extraction and purification of taxanes from plant matter, both from the standpoint of exposure of these chemicals to personnel who carry out these procedures and from the standpoint of the potential exposure of patients to these chemicals via trace amounts not removed from the purified taxanes in the final dosage form of the taxane medications.

V. Senilh et al, *Journal of Natural Products*, Vol. 46, No. 1, pp. 131–137 (1984) refers to the purification of taxol and cephalomannine from the trunk of *Taxus baccata* L. The purification method which is reported by Senilh et al. is deficient in that further purification of specific taxanes using HPLC or crystallization is required even after multiple elutions of taxanes on a variety of normal phase chromatography packings has been performed.

There have been attempts to isolate taxanes from plant matter using reverse phase column chromatography protocols. See, e.g., Keith M. Witherup et al., *Journal of Natural Products*, Vol. 53, No. 5, pp. 1249–1253 (1990); Keith M. Witherup et al., *Journal of Liquid Chromatography*, Vol. 12, No. 11, pp. 2117–2132 (1989). These attempts are undesirable in that the taxanes are isolated in relatively low yield, approximately 50% based upon the theoretical yield of taxanes.

Reverse phase column chromatography entails the use of a nonpolar column packing to effect molecular separation. Another disadvantage of reverse phase chromatography is the difficulty in separating taxanes from the aqueous elution medium. The evaporation of an aqueous medium is both expensive and time consuming. Furthermore, the use of an aqueous medium hydrolyzes labile bonds, thereby lowering the yield of taxanes. Also, the aqueous medium used in the reverse phase chromatography step partially epimerizes the C-7 stereocenter. The epimers so produced are undesirable in that they have diminished pharmacological properties. Furthermore, these undesirable epimers are separated from pharmacologically useful taxanes only with additional expense and difficulty.

Separation is further complicated because desired taxane products coelute during the reverse phase chromatography step. Additional chromatography steps must therefore be performed to completely separate the taxanes, resulting in increased expense and effort.

Another shortcoming of known methods for isolating taxanes from plant matter is that the methods require that the plant matter be in substantially desiccated form. Present methods of drying plant matter promote the degradation of taxanes contained within the plant matter. Drying plant matter, therefore, contributes to decreased taxane yields.

SUMMARY OF THE INVENTION

In accordance with the present invention, there are provided novel renewable sources of taxanes from cultivated varieties of Taxus plants in contrast to wild plants which are a limited resource. Preferably, the plants to be processed for taxane extraction are provided as intact clippings wherein a substantial amount of foliage is attached to the stems. The plant matter is subsequently treated with one or more solvents to obtain a taxane-rich composition.

This invention also provides a taxane-rich composition which is prepared from one or more cultivars of ornamental Taxus plants. The taxane-rich composition is prepared by treating the plant matter from one or more cultivars, provided as intact clippings, with one or more solvents to obtain the taxane-rich product. Prior to solvent treatment the plant matter optionally may be subjected to a drying step or may be ground.

In addition, this invention provides a process for preparing a plant material which can be used as a source for subsequent extraction of taxanes which process preserves taxane content and increases the accessibility of taxanes to extraction. This process comprises providing intact clippings wherein a substantial amount of foliage is attached to the stems of taxane-containing plant matter, drying the intact clippings to reduce the volatile content of the clippings to produce substantially dry clippings, and recovering the substantially dry clippings. Preferably, the process of preparing the plant material is conducted at a temperature of less than about 70° C. and is not conducted under unobstructed direct sunlight.

The plant materials, which can be used as a source for taxanes, prepared according to the method of this invention which method comprises providing intact clippings, drying the intact clippings to reduce the volatile components to produce substantially dry clippings and recovering the substantially dry clippings are also a part of this invention.

This invention also relates to a process for obtaining a crude taxane mixture from taxane-containing plants. The process comprises an initial solvent treatment comprising the steps of:

A. extracting taxanes from plant matter by contacting the plant matter with an organic solvent and obtaining a substantially solvent-free first residue rich in taxanes;

B. partitioning the first residue between an organic solvent capable of dissolving the taxanes and an aqueous solvent which does not dissolve significant quantities of taxanes to produce an organic phase and an aqueous phase;

C. separating the organic phase from the aqueous phase and recovering the organic phase substantially free of the aqueous phase; and D. forming a second residue from the second organic phase; and subjecting said second residue to a finishing treatment.

Taxanes present in the second residue are further purified through a finishing treatment selected from either treatment E or F. Finishing treatment E comprises the steps of:

dissolving the second residue in a solvent which allows for the reversible attachment of the taxanes to a solid support, introducing a solid support to the solvent comprising the dissolved second residue and allowing the taxanes of the second residue to attach to said solid support, separating said solid support from the solvent, sequentially contacting the solid support with attached taxanes with a series of solvents which solvents have differing taxane eluting properties, and eluting a taxane-rich fraction from the solid support as the crude taxane mixture.

Finishing treatment F comprises partitioning the second residue between an aqueous mixture and a nonpolar nonmiscible organic solvent, wherein the aqueous mixture comprises a single phase of water and a polar organic solvent miscible with water which polar organic solvent is present in the aqueous mixture in an amount sufficient to allow the taxanes present in the second residue to enter the aqueous mixture, and recovering the crude taxane mixture from the aqueous mixture.

In addition to the process of preparing a crude taxane mixture, this invention also includes the crude taxane mixture compositions prepared according to the method disclosed herein.

This invention also provides a process for separating two or more taxanes including taxol and cephalomannine comprising the steps of:

providing a mixture comprising two or more taxanes in a solvent suitable for loading onto a normal phase chromatography column, loading the taxane comprising mixture onto a normal phase chromatography column packed with a solid support in a solvent suitable as a mobile phase, and separating the taxanes by eluting the normal phase chromatography column with a mobile phase having a sufficient polarity to separately elute taxol and cephalomannine.

Additionally, the present invention provides a process for separating taxol from cephalomannine using normal phase chromatography wherein a mixture of ethyl acetate and methylene chloride is used as the mobile phase.

A process for obtaining taxanes from taxane-containing plant matter and separating taxanes is also a part of this invention. This process comprises:

providing intact clippings wherein a substantial amount of foliage is attached to the stems of taxane-containing plant matter, drying the intact clippings to reduce its volatile content to produce substantially dry clippings and recovering said substantially dry clippings, extracting taxanes from said substantially dry clippings according to the following steps comprising:

A. contacting the plant matter with an organic solvent and obtaining a substantially solvent-free first residue rich in taxanes;

B. partitioning the first residue between an organic solvent capable of dissolving the taxanes and an aqueous solvent which does not dissolve significant quantities of taxanes to produce an organic phase and an aqueous phase;

C. separating the organic phase from the aqueous phase and recovering the organic phase substantially free of the aqueous phase;

D. forming a second residue from the second organic phase;

subjecting said organic phase to a finishing treatment selected from either

E. dissolving the second residue in a solvent which allows for the reversible attachment of the taxanes unto a solid support, introducing a solid support to the solvent comprising the dissolved second residue and allowing the taxanes of the second residue to attach to said solid support, separating said solid support from the solvent, sequentially contacting the solid support with attached taxanes with a series of solvents which solvents have differing taxane eluting properties, and eluting a taxane-rich fraction from the solid support as the crude taxane mixture, or F. partitioning the second residue between an aqueous mixture and a nonpolar nonmiscible organic solvent, wherein the aqueous mixture comprises a single phase of water and a polar organic solvent miscible with water which polar organic solvent is present in said mixture in an amount sufficient to allow the taxanes present in the second residue to enter the aqueous mixture, and recovering the crude taxane mixture from the second aqueous mixture, providing the crude taxane mixture obtained from either treatments E or F, said crude taxane mixture comprising two or more taxanes, in a solvent suitable for loading onto a normal phase chromatography column;

loading the taxane comprising mixture onto a normal phase chromatography column packed with a solid support in a solvent suitable as a mobile phase;

separating the taxanes by eluting the normal phase chromatography column with a mobile phase having a sufficient polarity to separately elute taxol and cephalomannine.

Accordingly, it is an object of this invention to provide a consistent and renewable source of taxanes and method for efficiently recovering taxanes.

It is a further object of this invention to provide a method for the isolation of taxanes from plant matter that reduces the need for multiple elutions on a variety of normal phase chromatography packings.

It is an additional object of this invention to provide a method for the isolation of taxanes which method avoids or minimizes the use of certain chlorinated hydrocarbons such as methylene chloride and chloroform.

It is also an object of this invention to provide a method for the isolation of taxanes from plant matter that produces taxanes in high yields.

It is another object of this invention to provide a method for the drying of taxane-containing plant matter that minimizes loss of taxanes. Another object of this invention is to provide substantially dry plant materials which can be used as a source for taxanes.

It is a further object of this invention to provide a method for the isolation of taxanes from plant matter that permits the use of simple agitation to remove the organic components from the plant matter.

It is also an object of this invention to provide a method for the isolation of taxanes from plant matter that eliminates the need for filtration steps.

It is an additional object of this invention to provide a method for the isolation of taxanes from plant matter that does not require the use of aqueous elution media as found in reverse phase chromatography.

It is a further object of this invention to provide a method for the isolation of taxanes from plant matter that prevents the epimerization of C-7 stereocenter.

It is an additional object of this invention to provide a method for the isolation of taxanes from plant matter in which all taxanes possess substantially distinct retention times in normal phase chromatography.

It is another object of this invention to provide a method for obtaining a crude taxane mixture.

It is a further object of this invention to provide a composition comprising a crude taxane mixture.

DETAILED DESCRIPTION OF THE INVENTION

Any plant matter which contains taxanes is useful in the methods of the present invention. Furthermore, the plant matter used may be of pure genetic origin, mixed genetic or hybrid origin, or unknown genetic origin. Plant matter harvested from plants growing in the wild may be used as a source for taxanes. Examples include *T. brevifolia, T. baccata, T. cuspidata,* and *T. wallachiana.* Preferably, plant matter from cultivars of plants belonging to the genus Taxus is used as a source for taxanes and in particular certain varieties or species of cultivated ornamental Taxus. As used herein, "cultivars" means an assemblage of cultivated plants which is clearly distinguished by any characters (morphological, physiological, cytological, chemical, or others), and which when reproduced (sexually or asexually), retains its distinguishing characters. *Hortus Third: A Concise Dictionary of Plants Cultivated in the United States,* MacMillan Publishing Co., Inc., 1976.

Surprisingly, it has been discovered that several varieties of ornamental Taxus cultivars have been identified with taxol content in the fresh leaves comparable to or higher than that of the dried stem bark of *T. brevifolia.* Among the identified varieties are: *T.* X *media* "Henryi', *T.* X *media* 'Runyan', *T. cuspidata, T.* X *media* 'Halloran', *T.* X *media* 'Hatfield', *T.* X *media* 'Hicksii', *T.* X *media* 'Nigra', *T.* X *media* 'Tauntonii', *T.* X *media* 'Dark Green Spreader' and cultivated *T. cuspidata* 'Brevifolia', *T. cuspidata* 'Spreader'. Other varieties with taxol content in the dried leaves comparable to that of the dried stem bark of *T. brevifolia* include *T.* X *media* 'Wardii', *T.* X *media* 'Brownii', and *T.* X *media* 'Densiformis'.

Preferred cultivars may be selected from the group consisting of *T.* X *media* 'Densiformis', *T.* X *media* 'Hicksii', *T.* X *media* 'Dark Green Spreader', *T.* X *media* 'Runyan', *T.* X *media* Brownii', *T.* X *media* 'Wardii', *T.* X *media* 'Halloran', *T.* X *media* 'Hatfield', *T.* X *media* 'Nigra', *T.* X *media* 'Tauntonii', *T. cuspidata* 'Brevifolia', and *T. cuspidata.* Most preferably, however, are cultivars whose leaves have a higher taxane content than the dried stem bark of *T. brevifolia* are used as a source for taxanes. Most preferred cultivars may be selected from the group consisting of *T. cuspidata; T.* X *media* 'Halloran'; *T.* X *media* 'Hatfield'; *T.* X *media* 'Nigra'; *T.* X *media* 'Tauntonii'; *T.* X *media* 'Dark Green Spreader'; and *T.* X *media* 'Hicksii'. The cultivars stated above are available from commercial nurseries.

The plant matter used in the methods of this invention may be any portion of the cultivar that contains taxanes and may comprise the leaves, stems, branches, bark, roots or mixtures thereof. In the preferred embodiment of this invention, leaves are dried on the small stems as intact clippings prior to stripping in order to preserve their taxol content. As used herein, "intact clippings" is meant to include any clipping in which a substantial amount of the original foliage or leaves remains attached to the stems. A clipping is also referred to by those in the art as a "trimming". In addition, the taxol content of the small stems carrying the leaves is found to be approximately 60–70% of that of the leaves.

The plant matter to be extracted according to the methods of this invention is used in either fresh or dried form. As used herein, "fresh" is meant to include plant matter that retains substantially all of its volatile content. Preferably, the plant matter is dried at a temperature of less than about 70° C. under either fully lighted, shaded or dark conditions such that the drying is not conducted under unobstructed direct sunlight. As used herein, "fully lighted" is meant to include any condition in which ambient visible light, such as sunlight or that found in a greenhouse or artificially lighted building is not substantially blocked, reflected, or otherwise prevented from reaching the plant matter. More preferably, the plant matter is dried at a temperature of between about 65° C. and about 20° C. under shaded or dark conditions. Dry air or low humidity are preferred conditions for drying. Preferably the relative humidity is not above about 80%; more preferably not above about 50% relative humidity. As used herein, "shaded conditions" is meant to include an environment where between about 40% and about 70% of external unobstructed visible sunlight is blocked, reflected, or otherwise prevented from reaching the plant matter that is being dried. Alternatively, exposure of plant matter to light which light is absorbed by the plant and converted to heat, causing the temperature of the plant to rise above about 70° C. should be avoided. Preferably, at least a 25% reduction in the weight of the plant matter is obtained during the drying step. In a more preferred embodiment, the plant matter is dried until between about a 40% and about a 70% weight loss is obtained.

While not wishing to be bound by theory, it is believed that drying the plant matter under the conditions of this invention substantially preserves the taxane content of the plant matter by limiting their decomposition. In addition, it is also believed, while not wishing to be bound by any theory, that the method of drying the plant matter according to the present invention increases the accessibility of taxol and other taxanes to extraction.

Those of skill in the art will recognize that there is a relationship between the temperature of drying and the duration of drying. For example, drying at a relatively higher temperature will require a shorter period of time than drying at a relatively lower temperature. Any method of drying the plant matter to a weight loss as described above, while leaving the taxane content of the plant matter substantially unaffected, is within the scope of this invention. Such methods may include freeze-drying and microwave drying.

While the pressure at which the plant matter is dried is not deemed to be critical, it is understood that the use of decreased atmospheric pressure can promote drying at lower temperatures or shorter periods of time. The practitioner may therefore make a selection among various temperatures and atmospheric pressures of drying without departing from the scope of this invention.

Plant matter, prepared according to the process of this invention, comprising substantially dry intact clippings provide a plant material also a part of this invention which can be used as a source for taxanes. Following the drying step, the clippings are recovered for subsequent use as a source of taxanes.

While the plant matter to be extracted may be used in substantially intact form, it is preferably manipulated to increase the surface area of the plant matter and thereby increase the rate of taxane extraction. More preferably, the plant matter is cut, crushed or manipulated to form a powder. Most preferably, the plant matter is ground either by hand or by mechanical means. Suitable methods of grinding include the use of a blender, ball mill grinder, Wiley Mill or Fritz Mill. Other grinding apparati and methods may be used without departing from the scope and spirit of this invention.

Preferably, the plant matter is ground to a particle size of between about 40–80 mesh. More preferably, the plant matter is ground to a particle size of about 60 mesh.

To extract the taxanes, the fresh or dried plant matter to be extracted, in any physical form described above, is subjected to one or more initial solvent treatments comprising contacting the plant matter with an organic solvent to form an extract from which a substantially solvent-free first residue rich in taxanes may be obtained. Multiple extractions of the plant matter with the organic solvent may enhance taxane extraction. Preferably, the weight:volume ratio of plant matter to organic solvent ranges from about 1:8 to 1:12. A more preferred weight:volume ratio is about 1:10. A weight:volume ratio of plant matter to total volume of organic solvent used to extract the plant matter ranges from about 1:10 to about 1:150. A more preferred weight:volume ratio of plant matter to total volume of organic solvent is about 1:40.

Preferably, contact of the plant matter with the organic solvent is promoted by percolation or soxhlet extraction. More preferably, contact is promoted by shaking. Most preferably, contact is accomplished by agitating the plant matter as it soaks in the organic solvent. In this step, substantially all of the extractable organic matter, including taxanes, is removed from the plant matter and carried into the organic solvent.

The organic solvent which is contacted with the plant matter is preferably one commonly used with extracting organic chemicals from plant matter. Preferred organic solvents include ethanol, acetone, ethyl acetate, methylene chloride, methanol, methyl ethyl ketone, methyl isobutyl ketone, methyl t-butyl ether, or mixtures thereof. Preferably the organic solvent is ethanol. Furthermore, it has been found that between about three to about six volumes of between about 40 ml and about 200 ml of the organic solvent, applied sequentially over a period of about 8 hours to about 48 hours, are sufficient to remove essentially 100% of all taxanes from about 10 grams of plant matter. Also, it has been found that between about three to about six volumes of between 2 liters and about 5 liters of the organic solvent, applied sequentially over a period of about 8 hours to about 48 hours are sufficient to remove essentially 100% of all taxanes from about 1000 g of plant matter.

In a separate preferred embodiment, the plant matter is optionally first defatted with hexane, hexanes, pentane, petroleum ether, isooctane, or mixtures thereof, followed by contacting the plant matter with the organic solvent. For example, it has been found that the use of two volumes of approximately 100 ml hexane is sufficient to defat about 10 grams ground, dried plant matter over a period of between about eight hours and about two days.

In a more preferred embodiment the plant material is first defatted with hexane then extracted by shaking with the organic solvent, ethanol, acetone or ethyl acetate, for a period of 24 hours, changing the solvent four times during this period.

Those of skill in the art will recognize that the multiple uses of relatively smaller volumes of solvent is more effective in extracting materials than the single use of a large solvent volume. Thus, the practitioner may depart from the solvent volumes used in each of the steps involving extracting, partitioning, or otherwise removing organic materials described herein, as well as the number of iterations of extraction, without departing from the scope of the invention.

Hydrophilic moieties extracted from the plant matter by the organic solvent are then separated from the taxanes and removed by partitioning the extracted plant matter obtained from the organic solvent between a suitable pair of organic and aqueous solvents such that the taxanes remain in an organic solvent and the hydrophilic moieties are removed in an aqueous solvent. Organic and aqueous solvents which are immiscible with one another and may be separated from each other following partitioning to the extent that the purity of one phase is not substantially contaminated by the other, are suitable, provided that the taxanes have sufficient solubility in the organic solvent to remain in the organic solvent. Furthermore, the suitable aqueous solvents should not dissolve significant quantities of taxanes. Accordingly, in this and any subsequent step involving the partitioning of the taxanes between two different phases or their further purification, any solvent from a previous step remaining with the taxanes being purified, which solvent interferes with the action of solvents in a subsequent step is removed. For example, a solvent from one step which interferes with the partitioning of an organic and an aqueous solvent in a subsequent step by increasing the miscibility of the organic and aqueous solvents, is removed prior to contacting the taxanes with the organic and aqueous solvents to be partitioned.

Preferably, following extraction of the plant matter with the organic solvent, the extract is evaporated to dryness forming a first residue, with or without heating to promote the rate of solvent evaporation. If heating is used, the temperatures which promote epimerization of the taxanes should be avoided. Preferably, temperatures should not exceed about 35° C. to about 40° C.

Once the solvent has been evaporated, the material remaining as the first residue is dissolved in an organic solvent such as methylene chloride or, more preferably, ethyl acetate to form a second extract. A weight:volume ratio of first residue to organic solvent of about 1 to about 10 to 20 is preferred. For example, one gram of residue would be dissolved in about 10 to 20 ml of organic solvent. The second extract is washed by partitioning with an aqueous solvent component which does not dissolve significant quantities of taxanes to remove any hydrophilic moieties that may remain in the second extract. Water, similar polar solvents or mixtures thereof are suitable as the aqueous solvent. Preferably the aqueous solvent is water. A volume of aqueous solvent of about one half of that of the organic solvent is generally sufficient to wash the second extract. The aqueous solvent is then separated from the second extract. The aqueous solvent may be discarded.

The second extract, contains the taxanes. The second extract is optionally treated with a drying agent to remove water found in the extract, followed by removal of the drying agent and solvent evaporation to form a second residue. Preferred drying agents are anhydrous magnesium sulphate, 4 Å molecular sieves, calcium chloride or mixtures thereof. A more preferred drying agent is anhydrous sodium sulphate. The practitioner may find it advantageous to add a small volume of an organic solvent to the drying agent before combining the taxane containing second extract and the drying agent. Adding an organic solvent to the drying agent tends to prevent taxanes from adhering to the drying agent, and thereby improves yields. The drying agent may be removed by gravity filtration, vacuum filtration, or by decanting the solvent from the drying agent Another method to remove residual water from the second extract is to cool the second extract to a temperature at which the water in the second extract is in the frozen state without freezing the organic solvent. The liquid nonaqueous material could then be decanted separating it from the aqueous material.

Further purification of the taxanes is accomplished according to the invention by subjecting the second residue to a finishing treatment. According to the method of one finishing treatment, the second residue is dissolved in a solvent which allows for the reversible attachment of the taxanes onto a solid support. A solid support is then introduced into the solvent comprising the dissolved second residue and components from the second residue including the taxanes are allowed to attach to the solid support. Following separation of the solid support from the solvent, preferably by evaporating the solvent so as to leave a residue on the celite, which residue forms a coating comprising the taxanes, the solid support is sequentially eluted with a series of solvents which results in the elution of a taxane rich fraction. An example of a suitable solid support is celite. Preferably the celite is coated with components of the second residue which have been dissolved in an organic solvent comprising a mixture of methanol and ethyl acetate by evaporating the solvent from the mixture of solvent, second residue and celite. Preferably the methanol and ethyl acetate are present in a volume-volume ratio of 1:3.

The coated celite is preferably eluted first with hexane which does not significantly elute the taxanes but elutes other less polar molecules. A crude taxane mixture of the present invention is then eluted from the celite preferably with methylene chloride or another similarly polar solvent.

Another finishing step to further purify the taxanes present in the second residue comprises partitioning the second residue between an aqueous mixture and a nonpolar nonmiscible organic solvent. Preferably, the second residue is first dissolved in the aqueous mixture which is then combined with the nonpolar nonmiscible organic solvent. Preferred nonpolar nonmiscible organic solvents are such solvents as hexane, pentane, petroleum, ether, heptane, iso-octane, and mixtures thereof. Preferably, the nonpolar nonmiscible organic solvent is hexane. A preferred ratio of nonpolar nonmiscible organic solvent to aqueous mixture is 2 to 1. The aqueous mixture is a single phase aqueous mixture comprising water and a polar organic solvent miscible with water. The polar organic solvent is present in the aqueous mixture in an amount sufficient to allow the taxanes present in the second residue to enter into the aqueous mixture. Preferably, the aqueous mixture comprises more than about 50% polar organic solvent and the balance water. More preferably, the aqueous mixture comprises about 9 parts polar organic solvent and about 1 part water. In a preferred embodiment, the polar organic solvent is acetonitrile. In a more preferred embodiment, the polar organic solvent is methanol.

The aqueous mixture comprising the crude taxane mixture of the present invention is separated from the nonpolar nonmiscible organic solvent. The aqueous mixture may be evaporated to remove the polar organic component and the crude taxane mixture may be combined with an organic solvent to further purify the taxanes. Because the aqueous mixture is predominantly acetonitrile or methanol in composition, it is preferably evaporated directly to form a third residue comprising the crude taxane mixture. Heat, vacuum and combinations thereof may be used to promote evaporation, provided that the temperature of the aqueous mixture does not exceed about 40° C. The direct evaporation of the aqueous mixture avoids the possibility that any taxanes might be lost in unnecessary extraction steps.

Any of the foregoing initial solvent treatment steps or finishing treatment steps of the process to obtain the crude taxane mixture may be repeated one or more times. For example, any of the foregoing steps may be repeated at least one, two, three or four times.

Specific taxanes may be purified from the crude taxane mixtures of this invention by any commonly used purification protocols such as crystallization or trituration. Preferred taxanes which may be present in the crude taxane mixture and may be further purified according to the methods of this invention include taxol, cephalomannine, desacetylcephalomannine, baccatin III, 10-desacetyl baccatin III and 10-desacetyltaxol. Crystallization may be performed by allowing crystal formation from a substantially saturated solution of the crude taxane mixture. Alternatively, crystals may be grown by adding a seed crystal of the desired taxane product to a substantially saturated solution of crude taxanes. Ideally, a single solvent is used as the crystallization solvent, although the use of solvent mixtures is contemplated by this invention. The temperature of the crystallization solvent or solvents is not critical so long as substantially pure taxanes result.

According to the present invention, specific taxanes may also be purified from the crude taxane mixture using a series of normal phase chromatography columns. The specific taxanes are eluted by passing solvent mixtures having progressively increased elutrophic power through the columns. Generally, in normal phase column chromatography, the mobile phase comprises a two component system. The first component is a nonpolar organic solvent which controls the rate of compound elution. The second component is a polar organic solvent which elutes the compounds to be separated. Increasing amounts of the second component in the mobile phase generally decrease the contact time of the eluting compounds with the column packing. Higher concentrations of the second component therefore have the effect of decreasing the elution time.

The separation of taxanes may be improved by using a mobile phase that follows a gradient of increasing elutropic power, although isocratic elution is also contemplated by this invention. Preferred normal phase column chromatography packing materials for one or more of the chromatography columns may be selected from the group consisting of silica gel, florisil, alumina, and celite. A specifically preferred normal phase column chromatography packing material is silica gel 60, 230–400 mesh, manufactured by E. Merck, and available from Brinkman Instrument Co., Westbury, N.Y.

To prepare the crude taxane mixture, third residue, for running on a chromatography column, the third residue may be triturated (digested) repeatedly (1–5 times) with an organic solvent which dissolves the taxanes. Such an organic solvent may be selected from the group consisting of ether, methylene chloride, methanol, chloroform, ethyl acetate and acetone. The preferred organic solvent is methylene chloride. The third residue dissolved in the organic solvent is combined with a solid support such as diatomaceous earth or celite and evaporated to dryness, thereby adhering the taxanes to the solid support.

The taxane-containing solid support is then loaded directly onto the top of a packed normal phase chromatography column.

Once the solid support has been placed directly on top of the packed normal phase chromatography column, a mobile phase capable of separating the taxanes from one another and from other plant components is passed through the chromatography column. The mobile phase comprises (1) a nonpolar component selected from the group consisting of hexane, petroleum ether, iso-octane, and solvents having similar polarities, and (2) a polar component selected from acetone, ethyl acetate, ether, methyl t-butyl ether, chloroform, and solvents having similar polarities. Preferably, the mobile phase comprises hexane and acetone.

In a preferred embodiment, the mobile phase comprises initially between about 60% to 85% hexane and between about 15% to 40% acetone and follows a gradient of increasing elutropic power. The mobile phase can have any final composition so long as effective separation of taxanes is accomplished. Most preferably, however, the mobile phase has an initial concentration of about 75% hexane and about 25% acetone, and a final concentration of about 0% hexane and about 100% acetone. In the case of a hexane/acetone mixture, it is the hexane which controls the rate of elution and the acetone which elutes the taxanes. The desired taxanes are eluted from fractions comprising about 60% hexane and about 40% acetone, and about 0% hexane and about 100% acetone. Alternatively, any other series of solvent mixtures having polarities similar to those of the hexane/acetone mixtures described above are suitable to elute the taxane molecules from the first normal phase chromatography column.

Preferably, the normal phase chromatography column is run under pressure. For a 5×16 cm column containing 160 g silica gel 60 the flow rate is preferably about 100 ml/5 min.

The presence of taxanes in the fractions collected from the columns may be detected by thin layer chromatography ("TLC") using silica gel G $UV_{254}$ (Machery Nagel, Duren) using 5% methanol/chloroform as a developing system and p-anisaldehyde/sulfuric acid as a visualizing reagent. Taxol and cephalomannine appear as a bluish-grey spot with an $R_f$ value of 0.62 in the fractions eluted with hexane/acetone ratios of 60:40 and 55:45. Baccatin III appears as a blue spot with an $R_f$ value of 0.55 in the fractions eluted with hexane/acetone 50:50 and 45:55. The taxane 10-desacetyl baccatin III appears as a purplish spot with an $R_f$ value of 0.28 in the fraction eluted with hexane/acetone 0:100.

The hexane/acetone solvent from the taxane rich fractions is evaporated to dryness to form a taxane-rich product.

Further purification of the taxanes taxol and cephalomannine may be achieved by loading the taxane-rich product comprising taxol and cephalomannine onto another normal phase chromatography column comprising silica gel 60 or similar material packed with about 1% methanol and 99% methylene chloride. The elutropic power of the mobile phase is increased by increasing the concentration of methanol in increments of about 0.5% methanol, until the mobile phase has a composition of about 2.5% methanol, 97.5% methylene chloride. The mobile phase passing through a 2 cm×40 cm column preferably has a flow rate of about 8 ml/min. The taxanes, taxol and cephalomannine, are collected from fractions eluted with about 2.5% methanol and 97.5% methylene chloride. Alternatively, any other series of solvent mixtures having polarities similar to that of the methanol/methylene chloride solvent mixtures is suitable to elute the taxanes from the second normal phase chromatography column. The taxol-cephalomannine rich fractions from the methanol/methylene chloride column are evaporated to dryness to form another taxane-rich product.

Surprisingly, taxol may be separated from cephalomannine according to the method of the present invention by providing a mixture comprising two or more taxanes in a solvent suitable for loading onto a normal phase chromatography column. The taxane comprising mixture is then loaded onto a normal phase chromatography column packed with a solid support in a solvent suitable as a mobile phase. The taxanes, including taxol and cephalomannine are then separately eluted with a mobile phase having a sufficient polarity to separately elute taxol and cephalomannine. Preferably, a mixture of ethyl acetate and methylene chloride is used as the mobile phase. According to a preferred embodiment of the present invention, the second taxane rich product is dissolved in a mixture of about 20% ethyl acetate and 80% methylene chloride and loaded on a normal phase chromatography column packed with silica gel 60, or similar solid support as described above, in the presence of a mobile phase comprising about 20% ethyl acetate and 80% methylene chloride. The elutropic power of the mobile phase is increased by increasing the concentration of ethyl acetate in increments of about 5% ethyl acetate, until the mobile phase has a composition of about 50% ethyl acetate, 50% methylene chloride. A flow rate of about 8 ml/min is preferred for a 1 cm×32 cm column. Substantially, pure taxol is collected from fractions eluted with about 45% ethyl acetate, 55% methylene chloride. Substantially, pure cephalomannine is collected from fractions eluted with a mobile phase comprising about 50% ethyl acetate and 50% methylene chloride. Alternatively, any other series of solvent mixtures having polarities similar to those of the ethyl acetate/methylene chloride mixtures described above are suitable to elute the taxane molecules, taxol and cephalomannine, from the normal phase chromatography column.

Depending on the degree of separation of taxanes present in the crude taxane mixture achieved as a result of the initial normal phase chromatography step, additional chromatography of the taxanes using ethyl acetate and methylene chloride as the mobile phase, surprisingly, may separate and purify the taxanes, including the separation of taxol from cephalomannine, obviating the need for intermediate chromatography using methanol-methylene chloride.

Any of the foregoing chromatography steps may be repeated one or more times, for example one, two, three or four times, to further purify or separate the taxanes at a particular step.

Although column chromatography is a preferred method, any other chromatographic configuration, such as radial normal phase chromatography, as performed on a chromatotron, are useful in the methods of the present invention. Also, other suitable detection means may be used to identify taxanes without departing from the scope of the invention.

EXAMPLES

EXAMPLE 1

Quantification of Taxol Content of Different Varieties of Cultivated Ornamental Taxus The fresh leaves from clippings of various cultivated varieties of ornamental Taxus were analyzed for their taxol content following the procedure outlined below:

Extraction a. Leaves which had been stripped from clippings were well mixed and weighed.

b. Ten gram samples of each variety of cultivated ornamental Taxus were blended in a blender with 100 ml 95% ethanol, and the mixture transferred quantitatively into a 250 ml Erlenmeyer flask. The leaves and ethanol were allowed to extract by percolation for 24 hours, and then filtered with rinsing (1×25 ml). The percolation process was repeated three additional times.

c. The filtrates were combined (500 ml) and evaporated to dryness under vacuum at a temperature not exceeding 40° C. The weight of the ethanol extract, or first residue, was recorded.

Preparation of the Ethanol Extract for HPLC Analysis a. Approximately 100 mg of the extracts were weighed into screwcap vials. The caps were lined with a piece of aluminum foil to avoid contact of the extract with the cover-lining during partitioning.

b. The extracts were partitioned between water (1 ml) and methylene chloride (2 ml×5) or until the methylene chloride became colorless. The combined methylene chloride washes were pipetted into 25 ml Erlenmeyer flasks and evaporated to dryness to produce a second residue. The weight of the second residue was recorded.

c. The second residue was dissolved in ethyl acetate (5 ml) and methanol (2 ml) with sonication. Celite (200 mg to 650 mg) was introduced and allowed to be coated with the extracted material. The solvent was evaporated to dryness in vacuo to produce a celite material coated with the second residue.

d. The residue-coated celite was quantitatively transferred into a petri-dish. The dish was left under a hood until the last traces of solvent had been removed (10 minutes). The final product was triturated until a free flowing, uniform powder was obtained. The resulting powder was packed into a Pasteur pipet that served as a column.

e. The column was eluted with hexane (7 ml, or until the eluent was colorless), followed by methylene chloride (5–6 ml).

f. The methylene chloride eluent was evaporated in vacuo, and the weight of the remaining residue was recorded.

g. The remaining residue was dissolved with sonication in 1 ml methanol (HPLC grade). The solution was withdrawn in a 1 ml syringe and filtered through a Millex filtering unit (0.45µ) into a Wheaton vial, and capped.

HPLC Conditions

Column: µ Bondapak C-18 (10µ, Waters Associates)
Mobile Phase: methanol/water (65:35)
Flow rate: 1.2 ml/minute
Detection: U.V. at 227 nm
AUFS: 0.1
Amount injected: 10 µl.
Results of these analyses are shown in Table 1.

TABLE 1

Taxol Content in fresh leaves of certain Taxus Cultivars

| Cultivar | % Ethanol Extractives | % Taxol Average ± S. D.[1] |
|---|---|---|
| T. X media 'Henryi' | 17.63 | 0.0027[2] |
| T. X media 'Densiformis' | 18.93 | 0.0034[2] |
| T. X media 'Hicksii' | 15.43 | 0.0104[2] |
| T. X media 'Dark Green Spreader' | 15.32 | 0.0096[2] |
| T. X media 'Runyan' | 17.04 | 0.0057[2] |
| T. X media 'Brownii' | 19.55 | 0.0027[2] |
| T. X media 'Wardii' | 14.89 | 0.0052[2] |
| T. cuspidata 'Brevifolia' | 14.10 ± 0.36 | 0.0097 ± 0.0037 C. V. = 38% |
| T. X media 'Brownii' | 16.07 ± 0.93 | 0.00465 ± 0.00096 C. V. = 20.6% |
| T. cuspidata[5] | 14.73 ± 0.46 | 0.0141 ± 0.00226 C. V. = 16% |
| T. X media 'Densiformis' | 13.53 ± 1.36 | 0.00594 ± 0.00039 C. V. = 6.5% |
| T. X media 'Halloran' | 14.79 ± 0.18 | 0.01183 ± 0.00057 C. V. = 4.8% |
| T. X media 'Hatfield' | 12.83 ± 0.29 | 0.0121 ± 0.00042 C. V. = 3.5% |
| T. X media 'Hicksii' | 15.67 ± 0.29 | 0.0152 ± 0.0023 C. V. = 15% |
| T. X media 'Nigra'[4] | 15.13 ± 0.23 | 0.0291 ± 0.0057 C. V. = 19.6% |
| T. baccata 'Repandens' | 12.83 ± 0.57 | 0.00178 ± 0.00074 C. V. = 41.5% |
| T. X media 'Tauntonii'[3] | 16.47 ± 0.92 | 0.0198 ± 0.00245 C. V. = 12% |
| T. X media 'Hicksii' | 19.71 ± 1.01 | 0.0093 ± 0.0013 C. V. = 14% |
| T. X media 'Fairview' | 19.25 ± 0.38 | 0.0013 ± 0.0004 |

TABLE 1-continued

Taxol Content in fresh leaves of certain Taxus Cultivars

| Cultivar | % Ethanol Extractives | % Taxol Average ± S. D.[1] |
|---|---|---|
| T. X media 'Wardii' | 18.97 ± 0.45 | C. V. ± 30.7% 0.0084 ± 0.0036 |
| T. cuspidata 'Spreader' | 19.52 ± 0.49 | C. V. = 43% 0.0032 ± 0.00036 C. V. = 11% |

[1]n = 3, except for T. X media 'Hicksii', 'Fairview', C. V. = coefficient of variation. 'Wardii' and 'Spreader' where n = 4.
[2]Single values based on single determinations.
[3]Synonyms = 'Tautoni', T. cuspidata 'Tauntonii'
[4]Some authorities treat as T. baccata 'Nigra'
[5]Vegetatively propagated unnamed cultivar of T. cuspidata.

EXAMPLE 2

Effect on Taxol Recovery of Stripping Leaves from Stems before Drying Leaves

The fresh leaves (100 g) from clippings which were representative samples from large collections (3–6 lbs.) of certain cultivars were analyzed for their taxol content using the method described under Example 1. Table 2 shows the percent taxol extracted from fresh leaves compared to that extracted from dry leaves. The calculated taxol content is the % taxol expected in the dry plant material based on the % taxol content determined for the fresh material and the % moisture of the plant material. Percent Taxol (calculated)=% Taxol fresh/[1-(% moisture/100)]. The % moisture is determined from the difference in weight of the plant material before and after drying.

A ratio of found dry % taxol content to calculated dry % taxol content was then calculated (F/C). According to this calculation, a number less than 1.00 indicates a loss of taxol in the drying procedure (e.g., 0.90 indicates a 10% loss), and a number greater than 1.00 indicates that the drying method yields a quantity of taxol greater than is found by extracting fresh clippings (e.g., 1.20 indicates a 20% gain).

2(a) Fresh clippings of the same cultivars were separated into leaves and small stems. A portion (10 g) of the leaves of each cultivar were extracted and analyzed as described under Example 1. Results are shown in Table 2(a). Another portion of the leaves of each cultivar was allowed to dry at room temperature until no further weight loss was observed. A sample of the dried leaves was ground in a Wiley Mill, and a 10 g portion was extracted and analyzed as described under Example 1. The results are shown in Table 2(a).

2(b) Alternatively, clippings of T. X media 'Dark Green Spreader' were dried intact (i.e., without separating the leaves from their stems) at room temperature until no further weight loss was observed. The dried leaves were then stripped from their stems, ground in a Wiley Mill, and a 10 g portion was extracted and analyzed as described under Example 1. The results are shown in Table 2(b).

The data of Table 2(b) were obtained by analysis of 10 replicates of a large sample of plant material. The 131% retention in taxol content obtained according to the method in 2(b) compared with a mean 33% retention in taxol content obtained according to the method in 2(a) is reproducible. Surprisingly, drying according to the method of retaining the clippings intact enhances the recovery of taxol compared to ethanol extractions of leaves dried after they are stripped from their stems. An almost 4-fold increase in taxol retention occurs by drying the clippings intact as compared to drying after stripping the leaves.

TABLE 2

Taxol Content in Fresh and Dried Leaves of Certain Taxus Cultivars

| | Fresh Leaves | | | Dried Leaves | | | |
|---|---|---|---|---|---|---|---|
| Cultivar | % Ethanol Extractives | % Taxol | % Moisture | % Ethanol Extractives | % Taxol (Found) | % Taxol (Calculated) | F/C |
| a) | | | | | | | |
| 'Henryi' | 17.6 | 0.0028 | 62 | 17.0 | 0.0024 | 0.0073 | 0.33 |
| 'Densiformis' | 19.0 | 0.0035 | 61 | 23.5 | 0.0037 | 0.0089 | 0.42 |
| 'Hicksii' | 15.5 | 0.0104 | 63 | 17.3 | 0.0095 | 0.0281 | 0.34 |
| 'Dark green spreader' | 15.3 | 0.0096 | 64 | 20.0 | 0.0074 | 0.0267 | 0.28 |
| 'Runyan' | 17.0 | 0.0057 | 57 | 19.4 | 0.0036 | 0.0132 | 0.27 |
| 'Tauntonii' | 19.3 | — | 58 | 20.0 | 0.0057 | — | |
| 'Brownii' | 19.6 | 0.0027 | 58 | 17.3 | 0.0024 | 0.0064 | 0.38 |
| 'Wardii' | 14.8 | 0.0052 | 63 | 16.7 | 0.0032 | 0.0140 | 0.23 |
| b) | | | | | | | |
| 'Dark green spreader' | | 0.0088 ± 0.0025 | 64 | | 0.0320 ± 0020 | 0.0244 ± 0.0007 | 1.31 |

EXAMPLE 3

Determination of Taxol Content of Fresh Stems and Stripped Dried Stems

The percent taxol content of fresh stems (100 g) from clippings of certain cultivars was analyzed and compared to the percent taxol content of stems (10 g) which were dried and ground as described under Example 2(a). The fresh and ground stems were extracted and analyzed as described under Example 1. Results are shown in Table 3. The % taxol calculated was determined as described under Example 2. Also, the ratio of found dry % taxol content to calculated dry % taxol content (F/C) was determined as described under Example 2.

TABLE 3

Taxol Content in Fresh and Dried Leaves of Certain Taxus Cultivars

| Cultivar | Fresh Leaves | | | Dried Leaves | | | |
| --- | --- | --- | --- | --- | --- | --- | --- |
| | % Ethanol Extractives | % Taxol | % Moisture | % Ethanol Extractives | % Taxol (Found) | % Taxol (Calculated) | F/C |
| 'Henryi' | 11.2 | 0.0030 | 55 | 14.0 | 0.0029 | 0.0065 | 0.45 |
| 'Densiformis' | 11.8 | 0.0020 | 56 | 14.2 | 0.0047 | 0.0045 | 1.04 |
| 'Hicksii' | 9.2 | 0.0062 | 59 | 13.5 | 0.0108 | 0.0151 | 0.72 |
| 'Dark green spreader' | 8.6 | 0.0100 | 58 | 15.6 | 0.0010 | 0.0238 | 0.042 |
| 'Runyan' | 10.3 | 0.0043 | 50 | 11.2 | 0.0054 | 0.0086 | 0.63 |
| 'Tauntonii' | 12.5 | — | 52 | 17.9 | 0.0080 | — | — |
| 'Brownii' | 10.9 | 0.0009 | 51 | 13.1 | — | 0.0018 | — |
| 'Wardii' | 9.4 | 0.0043 | 58 | 11.3 | 0.0045 | 0.0102 | 0.44 |

EXAMPLE 4

(a) Determination of Taxol Content of Leaves of Nonstripped Barn-dried Clippings Fresh intact clippings (stems+leaves) of T. X media 'Densiformis' (Table 4(A)) and T. X media 'Dark Green Spreader' (Table 4(B)) were placed on aluminum wire cloth (18×16 inch, 0.010 gauge window screen) attached to a wooden frame. The frames were placed in a drying barn on supports 30" above the floor. The plant material was allowed to dry in the dark without additional heat. A fan provided air movement. The drying apparatus used is a "Roanoke" style model 7,5-I-G Bulk Curing Barn (Gregory Manufacturing Company, Inc., Lewistown, Woodville, N.C. 27849). The temperature ranged between 30° C. at 8 a.m. to 40° C. at 3:30 p.m. Drying lasted for 2 days. The moisture of the leaves prior to drying was determined to be 64.5% (T. X media 'Densiformis') and 66% (T. X media 'Dark Green Spreader') based on the difference in weight of the leaves before and after drying. Immediately before analysis, the dried leaves (10 gms) were recovered and stripped from their stems, ground using a Wiley mill, and extracted by percolation with ethanol, acetone or ethyl acetate. Analysis was carried out as described under Example 1.

The taxol content of the dried leaves was compared with fresh leaves of the same variety which were processed immediately after stripping by blending with the extraction solvent. Results are shown in Table 4. Calculated dry % taxol content was determined according to the method described under Example 2. A ratio of found dry % taxol content to calculated dry % taxol content (F/C) was then calculated according to the method described under Example 2.

(b) Determination of Taxol Content of Leaves of Nonstripped Greenhouse-dried Clippings Fresh intact clippings (stems+leaves) of T. X media 'Densiformis' and T. X media 'Dark Green Spreader' were placed on aluminum wire cloth (18×16 inch, 0.010 gauge window screen) attached to a wooden frame. The frames were placed on supports 30" above the floor. The plant material was allowed to dry in a polyethylene covered greenhouse (length 60', width 20' and height 9') approximately 55% shaded (using a shade fabric) and ventilated with two Arvin air coolers, fan only, without adding water to the cooling pads. The temperature ranged between 15.5° C. at 8 a.m. to 44° C. at 3:30 p.m. Drying lasted for 6 days. The moisture of the leaves prior to drying was determined to be 62% (T. X media 'Densiformis') and 66% (T. X media 'Dark Green Spreader') based on the difference in weight of the leaves before and after drying. The dried leaves were recovered and processed as in Example 4(a), and analyzed as described under Example 1. Results are compared with fresh leaves of the same cultivar and are shown in Table 4.

(c) Determination of Taxol Content of Leaves of Nonstripped Clippings Dried Outdoors under Shaded Conditions Fresh intact clippings (stems & leaves) of T. X media 'Densiformis' and T. X media 'Dark Green Spreader' were placed on aluminum wire cloth (18×16 inch, 0.010 gauge window screen) attached to a wooden frame. The frames were placed under a shade structure out of doors on supports 30" above the ground. The plant material was allowed to dry under a structure constructed by placing a shade fabric over a 2"×6" frame, approximately 7 feet above the ground. The shade fabric reduced ambient sunlight by about 80%. No fan was used. The temperature ranged between an average 22° C. at 8:00 a.m. to an average 36° C. at 3:00 p.m. Drying lasted for 10 days. The moisture of the leaves prior to drying was determined to be 63.3% (T. X media 'Densiformis') and 64% (T. X media 'Dark Green Spreader') based on the difference in weight of the leaves before and after drying. The dried leaves were recovered and processed as in Example 4(a), and analyzed as described under Example 1. Results are compared with fresh leaves of the same cultivar and are shown in Table 4.

(d) Determination of Taxol Content of Leaves of Nonstripped Clippings Dried Indoors at Room Temperature Fresh intact clippings (stems & leaves) of T. X media 'Densiformis' and T. X media 'Dark green Spreader' were placed on aluminum wire cloth (18×16 inch 0.010 gauge window screen) attached to a wooden frame and dried according to the procedure described under Example 2(b). The moisture of the leaves prior to drying was determined to be 63.3% (T. X media 'Densiformis') and 65% (T. X media 'Dark Green Spreader') based on the difference in weight of the leaves before and after drying. The leaves were recovered and processed according to the procedure described under Example 4(a), and analyzed according to the procedure described under Example 1. Results are compared with fresh leaves of the same cultivar and are shown in Table 4.

TABLE 4

COMPARISON OF THE TAXOL CONTENT OF FRESH LEAVES WITH
THAT OF LEAVES DRIED ON STEMS USING ETHANOL, ACETONE
AND ETHYL ACETATE AS THE SOLVENTS OF EXTRACTION

|  | Solvent | Found | Calculated Dry | F/C |
|---|---|---|---|---|
| A) | % Taxol (Average ± S. D.) *T. X media* 'Densiformis' | | | |
| Fresh Leaves | Ethanol | 0.0059 ± 0.0014<br>C. V. = 23.7% | — | — |
|  | Acetone | 0.0020 ± 0.0005<br>C. V. = 26% | — | — |
|  | Ethyl Acetate | 0.0030 ± 0.0004<br>C. V. = 13.3% | — | — |
| Barn-Dried | Ethanol | 0.0149 ± 0.0023<br>C. V. = 15.6% | 0.0166 ± 0.00081<br>C. V. = 15.6% | 0.88 |
|  | Acetone | 0.008 ± 0.0004<br>C. V. = 5% | 0.0056 ± 0.00013<br>C. V. = 4.6% | 1.43 |
|  | Ethyl Acetate | 0.0085 ± 0.0011<br>C. V. = 13.4% | 0.0084 ± 0.00038<br>C. V. = 12.8% | 1.00 |
| Greenhouse-Dried Leaves | Ethanol | 0.0165 ± 0.0022<br>C. V. = 13.7% | 0.0155 ± 0.00084<br>C. V. = 13.3% | 1.07 |
|  | Acetone | 0.0072 ± 0.00025<br>C. V. = 3.4% | 0.0052 ± 0.00010<br>C. V. = 3.5% | 1.39 |
|  | Ethyl Acetate | 0.0079 ± 0.0004<br>C. V. = 5.3% | 0.0079 ± 0.00016<br>C. V. = 5.5% | 1.00 |
| Shade-Dried Leaves | Ethanol | 0.0140 ± 0.0015<br>C. V. = 10.7% | 0.0160 ± 0.00056<br>C. V. = 11% | 0.86 |
|  | Acetone | — | — | — |
|  | Ethyl Acetate | — | — | — |
| Room Temperature-Dried Leaves | Ethanol | 0.0129 ± 0.0015<br>C. V. = 11.5% | 0.0160 ± 0.00054<br>C. V. = 11% | 0.79 |
|  | Acetone | — | — | — |
|  | Ethyl Acetate | — | — | — |
| B) | % Taxol (Average ± S. D.) *T. X media* 'Dark Green Spreader' | | | |
| Fresh Leaves | Ethanol | 0.0088 ± 0.0025<br>C. V. = 28% | — | — |
|  | Acetone | 0.0046 ± 0.0019<br>C. V. = 41% | — | — |
|  | Ethyl Acetate | 0.0060 ± 0.0012<br>C. V. = 20% | — | — |
| Barn-Dried | Ethanol | 0.0340 ± 0.0030<br>C. V. = 8.8% | 0.0216 ± 0.00124<br>C. V. = 9.7% | 1.57 |
|  | Acetone | 0.0192 ± 0.0075<br>C. V. = 3.9% | 0.0113 ± 0.00028<br>C. V. = 3.6% | 1.70 |
|  | Ethyl Acetate | 0.0169 ± 0.0012<br>C. V. = 13.4% | 0.0147 ± 0.00052<br>C. V. = 7.8% | 1.12 |
| Greenhouse-Dried Leaves | Ethanol | 0.0378 ± 0.00398<br>C. V. = 10.5% | 0.0258 ± 0.001245<br>C. V. = 9.7% | 1.46 |
|  | Acetone | 0.0162 ± 0.00085<br>C. V. = 5.3% | 0.0135 ± 0.00028<br>C. V. = 5.3% | 1.17 |
|  | Ethyl Acetate | 0.0148 ± 0.0011<br>C. V. = 7.6% | 0.0176 ± 0.0004<br>C. V. = 8% | 0.83 |
| Shade-Dried Leaves | Ethanol | 0.0326 ± 0.00278<br>C. V. = 8.5% | 0.0244 ± 0.001047<br>C. V. = 8.9% | 1.33 |
|  | Acetone | — | — | — |
|  | Ethyl Acetate | — | — | — |
| Room Temperature-Dried Leaves | Ethanol | 0.0230 ± 0.0020<br>C. V. = 8.7% | 0.0251 ± 0.000715<br>C. V. = 8.9% | 0.91 |
|  | Acetone | — | — | — |
|  | Ethyl Acetate | — | — | — |

EXAMPLE 5

Solvent of Extraction

Fresh clippings of *T. X media* 'Hicksii' were stripped into leaves and small stems which were then left to dry at room temperature under conditions as described under Example 2(a). For analysis, a portion of dried leaves (10 g) was ground and then extracted by percolation (4×100 ml) with one of several organic solvents utilizing the procedure of Example 1. The moisture content of the fresh leaves was 63%. Analysis was carried out as described under Example 1. Results are shown in Table 5.

TABLE 5

Effect Of Different Solvents On The Selectivity Of
Extraction Of Taxol Using Dried Leaves Of
*T. X Media* Hicksii

| Solvent | % Extractives | % Taxol |
|---|---|---|
| Methylene chloride | 3.96 | 0.0064 |
| Methylene chloride/ethanol (1:1) | 21.80 | 0.0137 |

TABLE 5-continued

Effect Of Different Solvents On The Selectivity Of
Extraction Of Taxol Using Dried Leaves Of
T. X Media Hicksii

| Solvent | % Extractives | % Taxol |
| --- | --- | --- |
| Acetone | 12.80 | 0.0150 |
| Acetone/methylene chloride (8:2) | 10.20 | 0.0143 |
| Ethanol | 19.90 | 0.0121 |
| Ethyl acetate | 7.40 | 0.0136 |

EXAMPLE 6

Method of Extraction

Three methods of extraction were compared using two replicates in each instance. Leaves of T. X media 'Hicksii" were stripped from fresh clippings and allowed to dry at room temperature under conditions as described under Example 2(a). The dried leaves (10 gms) were then ground and extracted using acetone by percolation, under soxhlet conditions or by shaking (soaking with agitation). Extraction by percolation was performed according to the procedure described under Example 1. Extraction under soxhlet conditions was carried out using one portion (100 ml) of solvent for 12 hours, followed by exchanges with fresh solvent at four hour intervals; a total of 400 ml of solvent was used for each 10 g sample of plant material over the 24-hour period of extraction. Extraction by shaking (soaking with agitation) was carried out using the same schedule of solvent exchange as described under soxhlet conditions. The extracts were then processed and analyzed as described under Example 1. Extracts obtained from the percolation method of extraction were combined and analyzed; extracts obtained from the other two methods of extraction were analyzed at each step of the extraction process. Results are shown in Table 6.

Wiley Mill. Each ground portion was then extracted by percolation using a solvent selected from among ethanol, acetone and ethyl acetate and using the procedure described under Example 1.

(a) Partitioning of the First Residue of the Ethanol Extract between Water and Methylene Chloride A known weight of the residue of the ethanol extract was partitioned between water (1 ml) and methylene chloride (2 ml×5). The methylene chloride phase was then prepared and analyzed by HPLC according to the method described under Example 1. The results are shown in Table 7a.

(b) Partitioning of the First Residue of the Acetone Extract between Water and Methylene Chloride A known weight of the residue of the acetone extract was partitioned between water (1 ml) and methylene chloride (2 ml×5). The methylene chloride phase was then prepared and analyzed by HPLC according to the method described under Example 1. The results are shown in Table 7b.

(c) Partitioning of the First Residue of the Ethyl Acetate Extract between Water and Methylene Chloride A known weight of the first residue of the ethyl acetate extract was partitioned between water (1 ml) and methylene chloride (2 ml×5). The methylene chloride phase was then prepared and analyzed by HPLC according to the method described under Example 1. The results are shown in Table 7c.

TABLE 6

Evaluation of Use of Three Methods of Extraction on the Efficiency of
Recovery of Taxol from the Dried Leaves of Taxus X Media 'Hicksii'

| Method of Extraction | Wt of Extract | Analysis # | Taxol (g % dry wt) | | | | Total Taxol (g % wt) | Average ± S. D. | Coefficient of Variation |
| --- | --- | --- | --- | --- | --- | --- | --- | --- | --- |
| | | | Step 1 | Step 2 | Step 3 | Step 4 | | | |
| Percolation | 1.23 | 1 | — | — | — | — | 0.0134 | 0.0145 ± | 10.3% |
| | 1.38 | 2 | — | — | — | — | 0.0156 | 0.0015 | |
| Soxhlet | 1.40 | 1 | 0.0121 | 0.0018 | 0.0008 | 0.0007 | 0.0154 | 0.0158 ± | 3.8% |
| | 1.50 | 2 | 0.0130 | 0.0011 | 0.0013 | 0.0009 | 0.0163 | 0.0006 | |
| Shaking | 1.90 | 1 | 0.0185 | 0.0056 | 0.0034 | 0.0028 | 0.0303 | 0.0264 ± | 20% |
| | 1.65 | 2 | 0.0126 | 0.0045 | 0.0039 | 0.0015 | 0.0226 | 0.0054 | |

EXAMPLE 7

Partitioning of the First Residue between Water and Methylene Chloride

Fresh clippings of T. X media 'Nigra' were dried in a bulk tobacco curing barn according to the method described under Example 4(a). A portion of the clippings were ground using a Wiley Mill, then extracted by percolation using a solvent selected from among ethanol, acetone and ethyl acetate and using the procedure described under Example 1. Another portion of clippings was separated into leaves and stems, and the two portions were ground separately using a

TABLE 7

Effect of three different solvents and celite method of purification on percent recovery of taxol from leaves, stems and whole clippings of barn-dried *T. X media* 'Nigra'
Purification using celite

| | | 1 - EtOH Extraction | | | | | |
|---|---|---|---|---|---|---|---|
| (a) Organ | Anal. # | EtOH Yield (g) | EtOH Anal. (mg) | $CH_2Cl_2$ Phase (mg) | Hexane Wash (mg) | $CH_2Cl_2$ Wash (mg) | Taxol g % dry wt |
| Leaves | 1 | 2.724 | 100.34 | 38.48 | 18.79 | 9.62 | 0.039 |
| | 2 | 2.775 | 100.10 | 32.19 | 18.65 | 9.26 | 0.040 |
| Clippings | 1 | 2.388 | 100.89 | 36.31 | 18.71 | 9.80 | 0.026 |
| | 2 | 2.471 | 100.96 | 37.09 | 19.22 | 9.74 | 0.038 |
| Stems | 1 | 1.463 | 100.42 | 29.29 | 12.75 | 7.29 | 0.012 |
| | 2 | 1.447 | 100.76 | 31.96 | 12.60 | 6.09 | 0.010 |

| | | 2 - Acetone Extraction | | | | | |
|---|---|---|---|---|---|---|---|
| (b) Organ | Anal. # | Acetone Yield | Acetone Anal. (mg) | $CH_2Cl_2$ Phase (mg) | Hexane Wash (mg) | $CH_2Cl_2$ Wash (mg) | Taxol g % dry wt |
| Leaves | 1 | 1.158 | 100.25 | 62.07 | 39.49 | 16.30 | 0.0268 |
| | 2 | 1.159 | 100.20 | 67.85 | 37.87 | 15.35 | 0.0266 |
| Clippings | 1 | 1.010 | 100.60 | 55.43 | 34.58 | 15.15 | 0.0217 |
| | 2 | 1.052 | 100.68 | 55.60 | 35.57 | 14.53 | 0.0226 |
| Stems | 1 | 0.755 | 100.44 | 41.87 | 17.67 | 8.23 | 0.0082 |
| | 2 | 0.755 | 100.46 | 44.39 | 17.05 | 9.65 | 0.0089 |

| | | 3 - Ethyl Acetate Extraction | | | | | |
|---|---|---|---|---|---|---|---|
| (c) Organ | Anal. # | ETOAC Yield | ETOAC Anal. (mg) | $CH_2Cl_2$ Phase (mg) | Hexane Wash (mg) | $CH_2Cl_2$ Wash (mg) | Taxol g % dry wt |
| Leaves | 1 | 0.801 | 100.02 | 67.31 | 47.59 | 16.74 | 0.0285 |
| | 2 | 0.777 | 100.23 | 66.48 | 44.77 | 17.39 | 0.0285 |
| Clippings | 1 | 0.648 | 100.70 | 79.91 | 48.74 | 22.57 | 0.0253 |
| | 2 | 0.639 | 100.72 | 69.15 | 42.48 | 20.86 | 0.0216 |
| Stems | 1 | 0.451 | 100.14 | 60.96 | 32.26 | 16.98 | 0.0118 |
| | 2 | 0.477 | 100.52 | 59.35 | 31.95 | 13.23 | 0.0103 |

EXAMPLE 8

Partitioning of the First Residue between Water and Ethyl Acetate followed by Second Solvent Partitioning between Hexane and an Aqueous Mixture Fresh intact clippings of *T. X media* 'Nigra' were dried in a bulk tobacco curing barn according to the method described under Example 4(a). A portion of the clippings was ground using a Wiley Mill, then extracted by percolation using a solvent selected from among ethanol, acetone and ethyl acetate and using the procedure described under Example 1. Another portion of clippings was separated into leaves and stems, and the two portions were ground separately using a Wiley Mill. Each ground portion was then extracted by percolation using a solvent selected from among ethanol, acetone and ethyl acetate and using the procedure described under Example 1.

(a) Partitioning of the First Residue of the Ethanol Extract between Water and Ethyl Acetate followed by Second Solvent Partitioning between Hexane and an Aqueous Mixture (Methanol:water)

A known weight of the residue of the ethanol extract was partitioned between water (1 ml) and ethyl acetate (2 ml×6). The ethyl acetate phase was evaporated and the second residue was then partitioned between two parts hexane and one part methanol:water (9:1). The methanol:water phase was evaporated to dryness in vacuo. The residue was dissolved with sonication in 1 ml methanol (HPLC grade) and the solution was withdrawn in a 1 ml syringe and filtered through a Millex filtering unit (0.45μ) into a Wheaton vial, and capped. HPLC analysis was then conducted as described under Example 1. Results are shown in Table 8a.

(b) Partitioning of the First Residue of the Acetone Extract between Water and Ethyl Acetate followed by Second Solvent Partitioning between Hexane and an Aqueous Mixture (Methanol:Water)

A known weight of the residue of the acetone extract was partitioned between water (1 ml) and ethyl acetate (2 ml×6). The ethyl acetate phase was evaporated and the second residue was then partitioned between two parts hexane and one part methanol:water (9:1). The methanol:water phase was evaporated to dryness in vacuo. The residue was dissolved with sonication in 1 ml methanol (HPLC grade) and the solution was withdrawn in a 1 ml syringe and filtered through a Millex filtering unit (0.45μ) into a Wheaton vial, and capped. HPLC analysis was then conducted as described under Example 1. Results are shown in Table 8b.

(c) Partitioning of the First Residue of the Ethyl Acetate Extract between Water and Ethyl Acetate followed by Second Solvent Partitioning between Hexane and an Aqueous Mixture (Methanol:Water)

A known weight of the residue of the ethyl acetate extract was partitioned between water (1 ml) and ethyl acetate (2 ml×6). The ethyl acetate phase was evaporated and the second residue was then partitioned between two parts hexane and one part methanol:water (9:1). The methanol:water phase was evaporated to dryness in vacuo. The residue was dissolved with sonication in 1 ml methanol (HPLC grade) and the solution was withdrawn in a 1 ml syringe and filtered through a Millex filter unit (0.45µ) into a Wheaton vial, and capped. HPLC analysis was then conducted as described under Example 1. Results are shown in Table 8c.

Comparison of Tables 7 and 8 indicates that purification by partitioning produces comparable yields of taxol when compared to the more expensive (in materials and labor) method of purifying using celite.

percolation with acetone. Analysis was carried out in duplicate using 10 g leaves. The acetone extract was treated and analyzed as described under Example 7(b), except that ethyl acetate was substituted for methylene chloride. Results are shown in Table 9.

TABLE 8

Effect of three different solvents and solvent partitioning method of purification on percent recovery of taxol from leaves, stems and whole clippings of barn-dried *T. X media* 'Nigra'
Purification using Partitioning

| | | 1 - Ethanol Extraction | | | |
| --- | --- | --- | --- | --- | --- |
| (a) Organ | Anal. # | EtOH Yield (g) | ETOAC Phase (mg) | Hexane Phase (mg) | MEOH/H$_2$O Phase (mg) | Taxol g % dry wt |
| Leaves | 1 | 100.21 | 42.85 | 12.21 | 31.13 | 0.039 |
|  | 2 | 100.80 | 40.46 | 10.50 | 29.00 | 0.030 |
| Clippings | 1 | 100.00 | 39.93 | 10.83 | 27.85 | 0.033 |
|  | 2 | 100.07 | 45.03 | 11.71 | 31.91 | 0.037 |
| Stems | 1 | 100.28 | 36.00 | 8.33 | 27.82 | 0.011 |
|  | 2 | 100.70 | 37.11 | 7.77 | 27.75 | 0.010 |
| | | 2 - Acetone Extraction | | | |
| (b) Organ | Anal. # | Acetone Anal (mg) | ETOAC Phase (mg) | Hexane Phase (mg) | MEOH/H$_2$O Phase (mg) | Taxol g % dry wt |
| Leaves | 1 | 100.18 | 69.56 | 31.19 | 38.14 | 0.0257 |
|  | 2 | 100.55 | 70.61 | 32.55 | 35.84 | 0.0290 |
| Clippings | 1 | 100.54 | 66.37 | 22.78 | 39.08 | 0.029 |
|  | 2 | 100.29 | 71.05 | 23.94 | 45.26 | 0.027 |
| Stems | 1 | 100.62 | 55.98 | 16.35 | 38.46 | 0.0093 |
|  | 2 | 100.31 | 53.04 | 15.11 | 36.94 | 0.0093 |
| | | 3 - Ethyl Acetate Extraction | | | |
| (c) Organ | Anal. # | ETOAC Anal (mg) | ETOAC Phase (mg) | Hexane Phase (mg) | MEOH/H$_2$O Phase (mg) | Taxol g % dry wt |
| Leaves | 1 | 100.07 | 81.26 | 37.98 | 39.40 | 0.027 |
|  | 2 | 100.90 | 86.04 | 42.32 | 44.30 | 0.026 |
| Clippings | 1 | 100.16 | 90.71 | 41.96 | 45.85 | 0.026 |
|  | 2 | 100.62 | 76.77 | 31.38 | 41.59 | 0.019 |
| Stems | 1 | 100.94 | 78.46 | 26.69 | 49.89 | 0.012 |
|  | 2 | 100.54 | 73.75 | 27.86 | 43.72 | 0.011 |

EXAMPLE 9

Elution of the Celite Column with Ethyl Acetate instead of Methylene Chloride

Fresh clippings of *T. X media* 'Hicksii' were separated into leaves and stems and allowed to dry at room temperature until no further weight loss was observed. The dried leaves were then ground using a Wiley Mill and extracted by

TABLE 9

Effect of partitioning of an acetone extract using water and ethyl acetate
and further purification on Celite using hexane and ethyl acetate as eluent
on the weight of each fraction and the final yield of taxol

| Analysis # | Yield of Extract (g) | Wt. of Extract Used for analysis (mg) | Wt. of ethyl acetate Phase (mg) | Wt. of hexane Wash (mg) | Wt. of ethyl acetate wash (mg) | Taxol (g % dry wt.) | Taxol Average ± S. D. |
|---|---|---|---|---|---|---|---|
| 1 | 1.241 | 104.20 | 65.67 | 28.09 | 30.96 | 0.0139 | |
| 2 | 1.257 | 100.68 | 57.90 | 26.92 | 25.20 | 0.0146 | 0.0142 ± 0.0005 C. V. = 3.5% |

EXAMPLE 10

(a) Defatting of the Plant Material Prior to Extraction by Percolation using Acetone A sample of leaves of *T. X media* 'Hicksii' was dried and ground using the method described under Example 9. Dried, ground leaves (10 g) were defatted with hexane by percolation for 2 days, changing the solvent every 24 hours (2×100 ml). The combined hexane extracts were evaporated to dryness (residue average 200 mg which represents 21% of the total hexane and acetone extractives). The marc (remaining residue) was transferred quantitatively into a 250 ml Erlenmeyer flask and extracted with acetone by percolation, changing the solvent every 24 hours for 4 days (4×100 ml). The combined acetone extracts were evaporated to dryness. A known weight of the acetone residue was partitioned between water (1 ml) and methylene chloride (2 ml×5). The methylene chloride phase was evaporated to dryness in vacuo and the residue reconstituted in methanol (1 ml). The methanolic solution was filtered through a Millex filtering unit, diluted 1:1 with methanol and used for HPLC analysis according to the method described under Example 1. Results are shown in Table 10.

(b) Defatting of the Plant Material Prior to Extraction by Soaking with Agitation (Shaking) using Acetone Dried, ground leaves (10 g) as in (a) were defatted with hexane by soaking with agitation for 8 hours, changing the solvent every 4 hours (100 ml×2). The average hexane extractives was 194 mg or 12% of the total hexane and acetone extractives. The marc was transferred quantitatively into a 250 ml Erlenmeyer flask and extracted with acetone (4×100 ml) by soaking with agitation over a 24 hour-period, changing the solvent at 12, 16, 20, and 24 hours. The extracts, collected at each point, were combined, evaporated to dryness in vacuo and a known portion of the resulting residue was partitioned between water (1 ml) and methylene chloride (2 ml×5). The methylene chloride phase was evaporated to dryness and the residue reconstituted in methanol (1 ml). The methanolic solution was filtered through a Millex filtering unit, diluted 1:1 with methanol and used for HPLC analysis. Results are shown in Table 10.

(c) Defatting of the Plant Material Prior to Extraction by Soxhlet using Acetone Dried, ground leaves (10 g) as in (a) were defatted with hexane by soxhlet extraction for eight hours, changing the solvent every four hours (100 ml×2). The average hexane extractives was 297 mg or 26% of the total hexane and acetone extractives. The marc, in the soxhlet, was further extracted with acetone (4×100 ml) according to the method described under Example 6. Extraction, partitioning and analysis are as described under Example 10(b) and the results are shown in Table 10.

TABLE 10

Effect of defatting on the Taxol content of dried leaves *T. X Media* 'Hicksii' using three different extraction methods

| Extraction Method | Analysis # | Hexane wt. (mg) (Defatting) | Yield of Extract (g) | Wt. of Extract used for Analysis (mg) | Methylene Chloride Phase (mg) | Taxol (g % dry wt.) | Taxol Average ± S. D. |
|---|---|---|---|---|---|---|---|
| Percolation | 1 | 205 | 0.963 | 102.96 | 48.26 | 0.0157 | 0.0174 ± 0.00247 |
| | 2 | 196 | 0.933 | 109.40 | 65.74 | 0.0192 | C. V. = 14.2% |
| Shaking | 1 | 193 | 1.12 | 102.54 | 38.28 | 0.0196 | 0.0263 ± 0.0095 |
| | 2 | 195 | 1.74 | 95.77 | 34.17 | 0.0330 | C. V. = 36% |
| Soxhlet | 1 | 332 | 0.838 | 97.25 | 44.83 | 0.0113 | 0.0117 ± 0.00063 |
| | 2 | 263 | 0.847 | 110.82 | 52.58 | 0.0122 | C. V. = 5.4% |

EXAMPLE 11

Partitioning of the Acetone Extract of the Defatted Plant Material between Water and Ethyl Acetate A sample of leaves of *T. X media* 'Hicksii' was dried and ground using the method described under Example 9. Dried, ground leaves (10 g) were defatted with hexane and extracted by percolation using acetone using the method described under Example 10(a). A known weight of the acetone residue was partitioned between water (1 ml) and ethyl acetate (2 ml×5). The ethyl acetate phase was evaporated to dryness in vacuo and the residue reconstituted in methanol (1 ml). The methanolic solution was filtered, diluted and analyzed as described under Example 10(a). Results are shown in Table 11.

TABLE 11

Effect of defatting, followed by extraction with Acetone then partitioning of the Acetone extract using ethyl acetate and water on the weight of every fraction and the final yield of Taxol in the dried stripped leaves of T. X media 'Hicksii'

| Analysis # | Hexane Wt. (mg) (Defatting) | Yield of Acetone Extract (g) | Wt. of Extract Used For Analysis (mg) | Wt. of Ethyl Acetate Residue (mg) | Taxol (g % Dry wt.) | Taxol Average ± S. D. |
|---|---|---|---|---|---|---|
| 1 | 196 | 0.960 | 105.71 | 65.38 | 0.0158 | 0.0163 ± 0.000707 |
| 2 | 195 | 0.914 | 109.78 | 66.13 | 0.0168 | C. V. = 4.3% |

EXAMPLE 12

Determination of Taxane Levels in T. X media 'Nigra' using a Solid Phase Finishing Treatment Fresh leaves of T. X media 'Nigra' (Rhode Island Nurseries, Newport, R.I.) were stripped from their stems, and the following procedures were carried out using three replicates. The stripped fresh leaves (10 gms) were placed in a Waring blender along with 100 ml of 95% ethanol to macerate the leaves. The leaves were ground for 2 minutes.

The ground leaves and the ethanol were quantitatively transferred to a 250 ml Erlenmeyer flask and the leaves were allowed to soak for 24 hours. The ethanol was filtered with rinsing (25 ml ethanol) and the ground leaves were returned to the Erlenmeyer flask, to which another 100 ml volume of 95% ethanol was added. This procedure was repeated three more times until a 500 ml volume of ethanol extract was obtained.

The ethanol extract was evaporated to dryness in vacuo at a temperature not exceeding 40° C. to leave a residue ("first residue"). The weight of this residue was 1.47 g±0.059 (C.V.=4%).

About 100 mg of the first residue was transferred into a 4 ml screwcap vial. The vial cap was lined with aluminum foil to avoid contact of the vial cap with the residue during subsequent partitioning steps.

The first residue was partitioned between about 1 ml of water and about five 2 ml volumes of methylene chloride. The methylene chloride was then transferred to a 25 ml Erlenmeyer flask and the solvent was evaporated in vacuo to form a second residue.

The residue from the methylene chloride layer was then dissolved in about 5 ml of ethyl acetate and about 2 ml of methanol. To assist in the dissolution of the residue the flask was sonicated. When the residue was completely dissolved, about 650 mg of celite was added. The residue was adhered to the celite by allowing the solvent to evaporate under reduced pressure to produce a coated celite material.

The coated celite was transferred to a petri dish, then triturated until a free-flowing powder was obtained. A Pasteur pipette was then packed with the triturated powder.

Hexane was washed through the column until the eluent appeared colorless (7 ml). Methylene chloride (5–6 ml) was then used to elute the taxanes. The methylene chloride was then evaporated in vacuo to produce the crude taxane mixture. The weight of this mixture was 39.1 mg±7.43 (C.V.=19%).

The crude taxanes were dissolved in 1 ml HPLC grade methanol. Sonication was used to assist in the dissolution of the crude taxanes. The solution was filtered through a Millex filtering unit (0.45μ) and collected in a flask.

The identity and amount of specific taxanes in the solution was determined using HPLC analysis from a 10 g sample. A μ Bondapak C-18 (10μ) column, obtained from Waters Associates was used for the HPLC analysis.

A mixture of methanol (65%) and water (35%) at a flow rate of 1.2 ml per min was used as the mobile phase. Taxanes were detected with a U.V. detector set at a wavelength of 227 nm.

The retention times and percent composition of the solution is shown below in Table 12.

TABLE 12

$R_t$ Values and Percent Composition of Specific Taxanes Isolated from T. X media 'Nigra'

| Taxane | $R_t$ Value (min.) | % Composition |
|---|---|---|
| Taxol | 11.5 | 0.291 |
| cephalomannine | 10.5 | — |
| baccatin III | 4.7 | — |
| 10-desacetyltaxol | — | — |
| 10-desacetylcephalomannine | — | — |
| 10-desacetyl baccatin III | 4.2 | — |

EXAMPLE 13

Percent Taxol Obtained from Barn-Dried Leaves Extracted According to the Method of Example 12

Fresh intact clippings of T. X media 'Nigra' leaves, still attached to their stems were placed on an aluminum wire cloth (18 in by 16 in, 0.10 gauge window screen) attached to a wooden frame inside a "Roanoak" style drying barn, model 7.5-1-G Bulk Curing Barn obtained from Gregory Manufacturing Company, Inc., of Woodville, N.C. The frames were placed on supports about 30 in. above floor level. The plant matter was dried in a ventilated barn in the dark.

During the drying step, the temperature varied between about 30° C. at 8 a.m. to about 40° C. at 3:30 p.m. Drying was continued for two days. The clippings were analyzed for taxane content following the procedure described in Example 12. The following taxanes were detected: taxol; cephalomannine; baccatin III; 10-desacetyl taxol; 10-desacetylcephalomannine; and 10-desacetyl baccatin III. The percent taxol present in the composition was 0.034.

EXAMPLE 14

Isolation of Taxol from the Leaves of T. X media 'Dark Green Spreader' using a Solid Phase Finishing Treatment Fresh clippings of T. X media 'Dark Green Spreader' were separated into leaves and small stems and then allowed to dry at room temperature according to the method described under Example 2(a). The dried leaves (500 g, showing a taxol content of 0.0074% as determined by the method described under Example 1) were ground in a Wiley Mill to a mesh size of about 60 and extracted by percolation with 95% ethanol, changing the solvent every 24 hours (1.5L×5). The combined ethanol extracts were evaporated on a Buchi rotary evaporator under reduced pressure at a temperature not exceeding about 40° C.

The ethanol residue (112 g, residue A) was partitioned between water (about 500 ml) and the following volumes of methylene chloride: one volume of about 1 liter, and three volumes of about 500 ml each. The methylene chloride layers were separated, combined and dried over anhydrous sodium sulphate. The drying agent was removed from the methylene chloride using vacuum filtration. The methylene chloride solvent was evaporated using a Buchi rotary evaporator under reduced pressure to produce a second residue (27.8 g, residue B).

The second residue (27.8 g) was dissolved in an ethyl acetate/methanol mixture (3:1, 600 ml) and the resulting solution divided into two 300 ml portions. Each portion was uniformly coated onto about 200 g celite 545 (Fisher) as described under Example 1.

The celite coated with the second residue, Residue B was packed into two columns (5×32 cm each) and each washed successively, under pressure, with hexane (2.2L) followed by methylene chloride (1.2L). Evaporation of the hexane and methylene chloride washes in vacuo yielded combined residues weighing 19.25 g (Residue C) and 6.35 g (Residue D), respectively.

Residue D comprising the crude taxane mixture (6.35 g) was dissolved in 250 ml ethyl acetate and adsorbed onto celite (50 g) according to the method described under Example 1. The resulting material was applied onto a silica gel 60 flash column (160 g, 5×16 cm, 230–400 mesh, E. Merck, 1 column volume=500 ml) packed in hexane/acetone (75:25). The polarity of the mobile phase was gradually increased to hexane/acetone (55:45) by increasing the percentage of acetone in 5% increments. Fractions were collected, under pressure, at a flow rate of 100 ml/5-minutes. The column was eluted with one column volume of hexane/acetone (75:25) collected as one 500 ml-fraction, followed by two column volumes of hexane/acetone (70:30) collected as 4 fractions 250 ml-each, two column volumes of hexane/acetone (65:35) as 4 fractions 250 ml-each, one column volume of hexane/acetone (60:40) as 2 fractions 250 ml-each, one column volume of hexane/acetone (55:45) as 10 fractions 50 ml-each. The collected fractions were examined by thin-layer chromatography on precoated silica gel G $UV_{254}$ (Machinery Nagel, Duren). Fractions eluted with hexane/acetone (60:40, 500 ml) and hexane/acetone (55:45, 150 ml) were combined and evaporated to dryness in vacuo (Fraction E, 0.427 g). In this fraction, 8 components were identified by thin layer chromatography using 5% methanol in chloroform as a developing system and p-anisaldehyde/sulfuric acid as a visualizing agent. The taxol-cephalomannine mixture appeared as a bluish-grey spot, with an $R_f$ value of 0.62.

Fraction E was further fractionated on a silica gel 60 flash column. The material (427 mg) was dissolved in 1% methanol/methylene chloride (2 ml) and applied onto a silica gel 60 column (55 g, 2×40 cm, 230–400 mesh, E. Merck, 1 column volume=120 ml), packed in 1% methanol/methylene chloride. The column was eluted, at low pressure to provide a flow rate of 8 ml/min., successively with 1% methanol/methylene chloride (2 column volumes as 20 fractions 12 ml-each), 1.5% methanol/methylene chloride (1 column volume as 10 fractions 12 ml-each), 2% methanol/methylene chloride (1 column volume as 10 fractions 12 ml-each) and 2.5% methanol/methylene chloride (3 column volumes as 74 fractions 5 ml-each). Fractions were monitored by thin layer chromatography using the same developing and visualizing reagent systems described above. The taxol-cephalomannine mixture was identified in fractions 78–86 eluted with 2.5% methanol/methylene chloride. These were combined and evaporated to dryness in-vacuo to give a residue (40.35 mg, Fraction F). This fraction when examined by HPLC indicated the presence of taxol together with cephalomannine.

Taxol was separated from cephalomannine by dissolving Fraction F (40.35 mg) in 1 ml of a solvent mixture of 20% ethyl acetate in methylene chloride and applying the solubilized Fraction F onto a silica gel 60 flash column (10 g, 1×32 cm, 230–400 mesh E. Merck, 1 column volume =21 ml) packed in the 20% ethyl acetate/methylene chloride solvent mixture. The column was eluted, at low pressure to provide a flow rate of 8 ml/min., successively with 20% ethyl acetate/methylene chloride (2 column volumes as 4 fractions 11 ml-each), 25% ethyl acetate/methylene chloride (1 column volume as 2 fractions 10 ml-each), 30% ethyl acetate/methylene chloride (1 column volume as 5 fractions 4 ml-each), 35% ethyl acetate/methylene chloride (2 column volumes as 9 fractions 4.5 ml each), 40% ethyl acetate/methylene chloride (1 column volume as 7 fractions 3 ml-each), and 45% ethyl acetate/methylene chloride (2 column volumes, as 20 fractions 2 ml-each). The fractions were monitored by thin-layer chromatography on silica gel G $UV_{254}$ using ethyl acetate/methylene chloride (1:1) as developing solvent and p-anisaldehyde/sulfuric acid as visualizing reagent. Taxol (26 mg) was obtained in a pure form, as determined by HPLC analysis, in fractions 35–50 eluted with 45% ethyl acetate in methylene chloride.

EXAMPLE 15

Isolation of Taxol from the Leaves of *T. X media* 'Nigra' using a Partitioning Finishing Treatment Step Intact clippings of *T. X media* 'Nigra' were barn-dried as described in Example 4(a). The leaves obtained from the barn-dried intact clippings (500 g, showing a taxol content of 0.043% dry weight as determined by the method of Example 1) were ground in a Wiley Mill to a mesh size of about 60 and treated by percolation with 95% ethanol (8L). The combined ethanol extracts were evaporated to dryness on a Buchi rotary evaporator under reduced pressure at a temperature not exceeding 40° C.

The ethanol residue (134.4 g, first residue, residue A) was partitioned between water (about 600 ml) and the following volumes of ethyl acetate: two volumes of about 1.2L, and three volumes of about 600 ml each. The ethyl acetate layers were separated, combined and dried over anhydrous sodium sulfate. The drying agent was removed from the ethyl acetate using vacuum filtration. The ethyl acetate solvent was evaporated using a Buchi rotary evaporator under reduced pressure to produce a second residue (44 g, Residue B).

Residue B was partitioned between a biphasic mixture of about 1 part water, 9 parts methanol (500 ml), and two volumes of hexane (1000 ml). Subsequently, each phase was washed with the opposite solvent (100 ml×5) and the washings combined with their respective phases. The combined hexane layers were evaporate to dryness to yield a reside (17.7 g, residue C) and the combined water/methanol layers were evaporated, in vacuo, to produce a residue of a crude taxane mixture (31.1 g, residue D).

Residue D (31.1 g) was washed with sonication using methylene chloride (300 ml×4). The methylene chloride washings were combined, and evaporated in vacuo to yield a methylene chloride soluble portion of Residue D (17.3 g, Residue E, showing a taxol content of 167 mg as determined by the method of Example (1)). The weight of the methylene chloride insoluble portion of Residue D was 13.8 g and showed a taxol content of 20 mg as determined by the method of Example 1.

Residue E (17.3 g) was dissolved in 250 ml ethyl acetate and adsorbed onto celite (30 g). The resulting material was applied onto a silica gel 60 flash column (315 g, 5×32 cm, 230–400 mesh, E. Merck, 1 column volume=600 ml) packed in hexane/acetone (70:30). The polarity of mobile phase was gradually increased to hexane/acetone (45:55) by increasing the acetone content in 5% increments and then the column washed with 100% acetone. Fractions were collected, under pressure, at a flow rate of 100 ml/5-minutes. The column was eluted with two column volumes of hexane/acetone (70:30) collected as eight fractions: 300 ml, 100 ml, 125 ml, 200 ml, 160 ml, 190 ml and 210 ml, followed by one column volume of hexane/acetone (65:35) collected as 2 fractions: 175 ml and 300 ml, one column volume of hexane/acetone (60:40) as one fraction 500 ml-fraction, one column volume of hexane/acetone (50:50) as 7 fractions 100 ml-each, one column volume of hexane/acetone (45:55) as 6 fractions: 100 ml-each, and 3 column volumes of 100% acetone as 4 fractions: 450 ml-each. The collected fractions were examined by thin-layer chromatography on precoated silica gel G UV$_{254}$ (Machery Nagel, Duren) using 5% methanol in chloroform as a developing system and p-anisaldehyde/sulfuric acid as a visualizing reagent.

Fractions eluted with hexane/acetone (55:45, 100 ml) and hexane/acetone (50:50, 450 ml) were combined and evaporated to dryness in vacuo (Fraction F, 1.61 g).

In this fraction, 8 components were identified using 5% it methanol in chloroform as a developing system and p-anisaldehyde/sulfuric acid as a visualizing reagent. Taxol-cephalomannine mixture appeared as a bluish-gray spot, with a R$_f$ value of 0.62.

While we have hereinbefore described a number of embodiments of this invention, it is apparent that the basic constructions can be altered to provide other embodiments which utilize the methods of this invention. Therefore, it will be appreciated that the scope of this invention is defined by the claims appended hereto rather than by the specific embodiments which have been presented hereinbefore by way of example.

We claim:

1. A crude taxane mixture from plant matter containing taxanes obtained according to the following steps:
    (a) separating intact clippings from live Taxus plants wherein said intact clippings include leaves attached to stems;
    (b) drying the intact clippings of step (a) at a temperature of between 20° C. and 70° C. to form dried plant matter;
    (c) contacting the dried plant matter from step (b) with an organic solvent, wherein the weight:volume ratio of plant matter to organic solvent ranges from 1:8 to 1:12, for a time sufficient to extract taxanes from the dried plant matter and obtaining a taxane-containing extract;
    (d) evaporating the taxane-containing extract formed in step (c) to form a residue and partitioning the residue between water and an organic solvent to form a two phase solution comprising a taxane-containing organic phase and a polar aqueous phase;
    (e) removing the polar aqueous phase from the taxane-containing organic phase;
    (f) evaporating the taxane-containing organic phase of step (e) to form a crude taxane mixture.

2. The crude taxane mixture of claim 1, wherein the plant matter is provided from one or more species of cultivars of the ornamental Taxus genus.

3. The crude taxane mixture of claim 2, wherein the ornamental Taxus cultivars are selected from the group consisting of *T. X media* Henryi, *T. X media* Halloran, *T. X media* Hatfield, *T. X media* Nigra, *T. X media* Densiformis, *T. X media* Hicksii, *T. X media* Dark Green Spreader, *T. X media* Runyan, *T. X media* Brownii, *T. X media* Wardii, *T. X media* Tauntonii, *T. X media* Fairview, *T. cuspidata* Brevifolia, *T. cuspidata*, and *T. cuspidata* Spreader.

4. The crude taxane mixture of claim 1, wherein the organic solvent of step (c) is selected from the group consisting of ethanol, acetone, ethyl acetate, methylene chloride, methanol, methyl ethyl ketone, methyl isobutyl ketone, methyl-t-butyl ether, and mixtures thereof.

5. The crude taxane mixture of claim 1, wherein the crude taxane mixture comprises taxanes selected from the group consisting of taxol, cephalomannine, desacetylcephalomannine, baccatin III, 10-deacetyl baccatin III and 10-desacetyltaxol.

* * * * *